United States Patent
Lee et al.

(10) Patent No.: US 8,849,583 B2
(45) Date of Patent: Sep. 30, 2014

(54) POLYMER SIDE CHAIN ANALYSIS METHOD AND POLYMER SIDE CHAIN ANALYSIS DEVICE

(71) Applicant: LG Chem, Ltd., Seoul (KR)

(72) Inventors: Seung Yup Lee, Daejeon (KR); Hye Sung Cho, Daejeon (KR); Jin Sook Ryu, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/238,647

(22) PCT Filed: May 15, 2013

(86) PCT No.: PCT/KR2013/004313
§ 371 (c)(1),
(2), (4) Date: Feb. 12, 2014

(87) PCT Pub. No.: WO2013/191380
PCT Pub. Date: Dec. 27, 2013

(65) Prior Publication Data
US 2014/0214338 A1    Jul. 31, 2014

(30) Foreign Application Priority Data

Jun. 18, 2012 (KR) .......................... 10-2012-0064919

(51) Int. Cl.
*G01N 31/00* (2006.01)
*G06F 17/18* (2006.01)
*G06F 19/00* (2011.01)

(52) U.S. Cl.
CPC .................... *G06F 19/708* (2013.01)

USPC .............................................. 702/27; 702/179

(58) Field of Classification Search
None
See application file for complete search history.

(56) References Cited

U.S. PATENT DOCUMENTS 7,056,744 B2 * 6/2006 DesLauriers et al. ........... 436/85
2011/0218308 A1 9/2011 Nozue et al.

FOREIGN PATENT DOCUMENTS

KR   1020110084217 A   7/2011

OTHER PUBLICATIONS

Khelil Slimani et al., "Determination of scission, crosslinking and branching parameters of electron beam irradiated methacrylate-acrylamide copolymer", Polymer Degradation and Stability 94 (2009), pp. 584-590.
L.I. Kulin et al., "Long and Short Chain Branching Frequency in Low Density Polyethylene (LDPE)", Pure & Appl. CHem., vol. 60, No. 9, pp. 1403-1415, 1988.
H. Mori et al., "Synthesis and Characterization of Branched Polyeletrolytes. 1. Preparation of Hyperbranched Poly (acrylic acid) via Self-Condensing Atom Transfer Radical Copolymerization", Macromolecules 2002, 35, 9270-9281.

* cited by examiner

*Primary Examiner* — John Breene
*Assistant Examiner* — Manuel Rivera Vargas
(74) *Attorney, Agent, or Firm* — McKenna, Long & Aldridge LLP

(57) ABSTRACT

The present disclosure relates to an apparatus and a method for analyzing side chains of a polymer. More specifically, the present disclosure relates to an apparatus and a method for analyzing the number of side chains of a polymer.

17 Claims, 9 Drawing Sheets

POLYMER SIDE CHAIN ANALYSIS METHOD AND POLYMER SIDE CHAIN ANALYSIS DEVICE

This application is a 35 USC §371 National Stage entry of International Application No. PCT/KR2013/004313, filed on May 15, 2013, which claims priority of Korean Application No. 10-2012-0064919, filed on Jun. 18, 2012, all of which are hereby incorporated by reference in their entirety.

TECHNICAL FIELD

This application claims priority to and the benefits of Korean Patent Application No. 10-2012-0064919, filed with the Korean Intellectual Property Office on Jun. 18, 2012, the entire contents of which are incorporated herein by reference.

The present disclosure relates to an apparatus and a method for analyzing side chains of a polymer. More specifically, the present disclosure relates to an apparatus and a method for analyzing the number of side chains of a polymer.

BACKGROUND ART

Physical properties of a polymer are affected mostly by a structure of a polymer, along with a molecular weight and an extent of molecular weight distribution. The simplest polymer structure is a linear structure. A linear structure literally refers to a shape in which a monomer that forms a polymer is bonded linearly to constitute a main chain. Various types of branched chains are possible, and side chains may be formed. These side chains can affect the physical properties of a polymer.

Of the above side chains, a long chain branch (LCB) may affect the strength of a polymer, the glass temperature, or the like.

Meanwhile, of the above side chains, an atactic short chain branch may reduce the strength of a polymer, since it makes a polymer arrangement poor.

It is thus important in analyzing the characteristics of physical properties of a polymer to identify the existence of side chains, which greatly affect physical properties of a polymer, and to accurately measure the number thereof.

The number of side chains that branches in a polymer may be measured through the linear correlation of a log scale graph of the molecular weight and the intrinsic viscosity, which is obtained by analyzing the polymer. In a log scale graph of the molecular weight and the intrinsic viscosity of a polymer having side chains, there is a critical point representing a maximum straight-line segment, to which the slope is constant as a straight line from the origin as in the graph of a linear polymer, and after which the slope decreases at a certain point. The more side chains exist within a polymer, the greater the difference in slope from the log scale graph of a linear polymer after a critical point representing a maximum straight-line segment.

Generally, as a method for computing the number of side chains of a polymer having side chains, the number of side chains of a polymer is computed using an area generated based on the difference from a reference graph after a critical point by comparing a log scale graph of a polymer having side chains with a log scale graph of a linear polymer as a reference.

At this time, accurately locating a critical point representing a maximum straight-line segment is important in order to compute the number of side chains of a polymer with high accuracy.

DISCLOSURE

Technical Problem

The present disclosure relates to an apparatus and a method for analyzing side chains of a polymer. More specifically, the present disclosure provides an apparatus and a method for analyzing the number of side chains of a polymer.

Technical Solution

One embodiment of the present disclosure provides a method for analyzing side chains of a polymer, including the steps of 1) displaying a log scale graph of the molecular weight and the intrinsic viscosity of a polymer;

2) calculating an explanatory power ($R^2$) value of a regression equation between a coordinate closest to an origin and a coordinate farthest from the origin or a coordinate closer to the origin than the coordinate farthest from the origin, among the total coordinates of the graph, and determining whether the value exceeds a previously set reference explanatory power ($R^2$) value of a regression equation; and 3) computing a critical point representing a maximum straight-line segment using the calculated explanatory power ($R^2$) value of the regression equation, if the calculated explanatory power ($R^2$) value of the regression equation exceeds the previously set reference explanatory power ($R^2$) value of the regression equation.

Another embodiment of the present disclosure provides a computer-readable recording medium on which a program for executing the method is recorded.

Still another embodiment of the present disclosure provides an apparatus for analyzing side chains of a polymer, including a display unit displaying a log scale graph of the molecular weight and the intrinsic viscosity of a polymer;

an analyzing unit calculating an explanatory power ($R^2$) value of a regression equation between a coordinate closest to an origin and a coordinate farthest from the origin or a coordinate closer to the origin than the coordinate farthest from the origin, among the total coordinates of the graph, and determining whether the value exceeds a previously set reference explanatory power ($R^2$) value of a regression equation; and a first computation unit computing a critical point representing a maximum straight-light segment using the calculated explanatory power ($R^2$) value of the regression equation, if the calculated explanatory power ($R^2$) value of the regression equation exceeds the previously set reference explanatory power ($R^2$) value of the regression equation.

Advantageous Effects

According to one embodiment of the present disclosure, there are advantages such that the presence or absence of side chains of a polymer can be seen even if the number of side chains of the polymer is small.

According to one embodiment of the present disclosure, there are advantages such that the number of side chains of a polymer can be computed even if the number of side chains of the polymer is small.

MODE FOR DISCLOSURE

Figure 1:
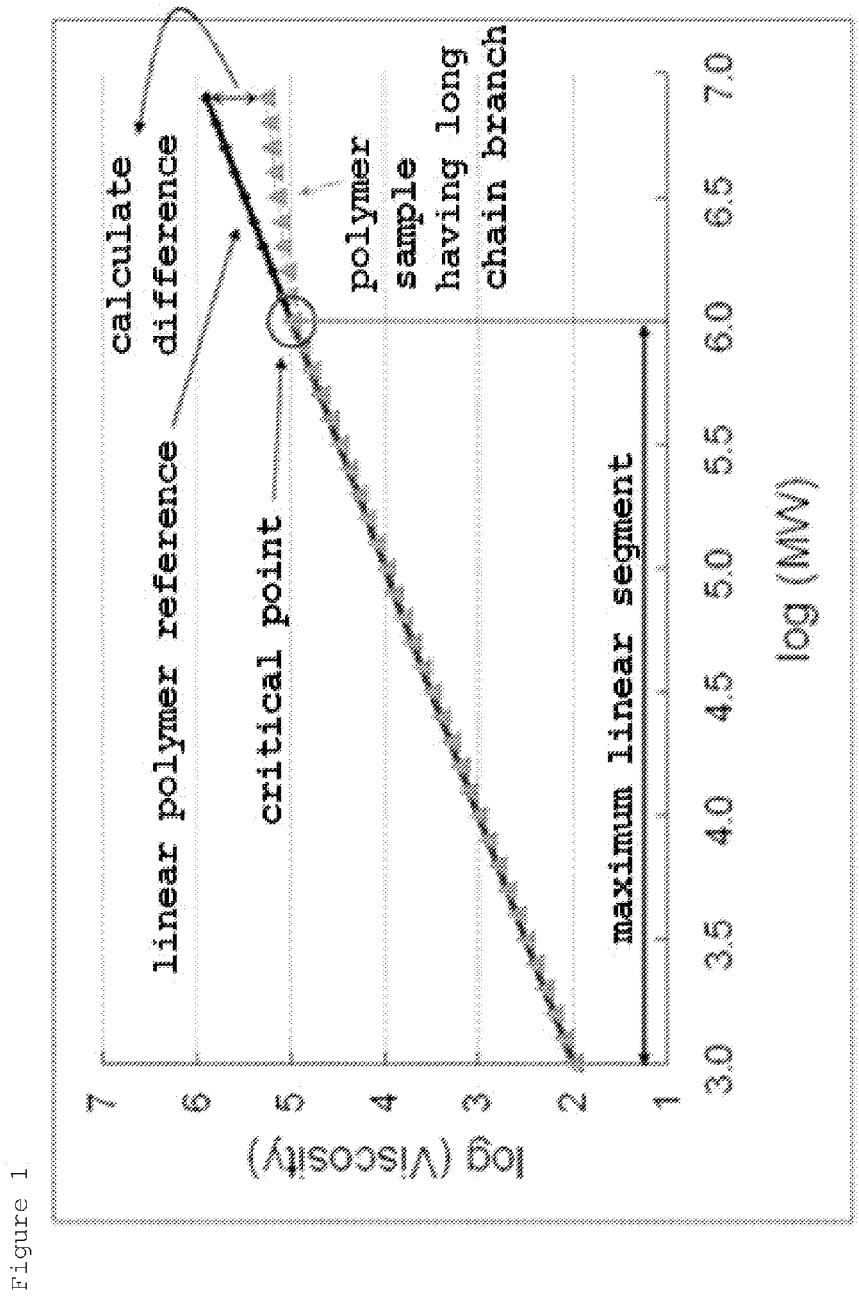
FIG. 1 is a diagram that shows a method for calculating the number of side chains of a polymer using the graph of a linear polymer as a reference.

Hereinafter, the present disclosure will be described in detail.

The present disclosure provides a method for analyzing the side chains of a polymer, including the steps of 1) displaying a log scale graph of the molecular weight and the intrinsic viscosity of a polymer;

2) calculating an explanatory power ($R^2$) value of a regression equation between a coordinate closest to an origin and a coordinate farthest from the origin or a coordinate closer to the origin than the coordinate farthest from the origin, among the total coordinates of the graph, and determining whether the value exceeds a previously set reference explanatory power ($R^2$) value of a regression equation; and 3) computing a critical point representing a maximum straight-light segment using the calculated explanatory power ($R^2$) value of the regression equation, if the calculated explanatory power ($R^2$) value of the regression equation exceeds the previously set reference explanatory power ($R^2$) value of the regression equation.

The graph in the Step 1) may be obtained by performing measurement using Gel Permeation Chromatography (GPC), however, the method is not limited thereto.

An explanatory power ($R^2$) of the regression equation used herein is a value indicating linearity when represented by a linear regression equation, and the explanatory power ($R^2$) value of the regression equation is 1 for a straight line that extends perfectly linearly, and the explanatory power ($R^2$) value of the regression equation less than 1 indicates poorer linearity.

An explanatory power ($R^2$) of the regression equation used herein indicates the case of a linear regression equation, and indicates how well the regression equation set explains the original data. An explanatory power ($R^2$) of the regression equation has a value between 0.0 and 1.0, and if the value is 1.0, it means that the linear regression equation perfectly explains the original values (the log scale graph of the molecular weight and the intrinsic viscosity) accurately. In other words, an explanatory power ($R^2$) of a regression equation equal to 1.0 indicates that the log scale graph of the molecular weight and the intrinsic viscosity shows a perfectly linear relationship.

The reference explanatory power ($R^2$) value of the regression equation previously set in the Step 2) may range from 0.9 to 0.9999, but is not limited thereto.

The Step 2) may include the steps of setting the explanatory power ($R^2$) value of the regression equation between the coordinate closest to the origin and the coordinate farthest from the origin as an initial value (A1);

calculating the explanatory power ($R^2$) value of the regression equation between the coordinate closest to the origin and a coordinate closer to the origin than the coordinate farthest from the origin, among the total coordinates of the graph, and determining whether the value is greater than the initial value (A1); and substituting the initial value (A1) for the calculated explanatory power ($R^2$) value of the regression equation, if the calculated explanatory power ($R^2$) value of the regression equation is greater than the initial value (A1).

Meanwhile, the step of maintaining the initial value (A1) may be included if the calculated explanatory power ($R^2$) value of the regression equation is not greater than the initial value (A1).

The Step 2) may include the step of calculating the explanatory power ($R^2$) value of the regression equation between the coordinate closest to the origin and a coordinate k points closer to the origin than the coordinate farthest from the origin when the number of coordinate data in the graph is N. In this case, k is an integer, and $1 \leq k \leq N$.

If the calculated explanatory power ($R^2$) value of the regression equation does not exceed the previously set reference explanatory power ($R^2$) value of the regression equation, the step of calculating the value of k/N and determining whether the value is the same as or greater than a previously set ratio value may be included.

If the calculated value of k/N is smaller than the previously set ratio value, the step of calculating the explanatory power ($R^2$) value of the regression equation between the coordinate closest to the origin and a coordinate k+1 points closer to the origin than the coordinate farthest from the origin may be included.

In this case, the number of data coordinates used to calculate the explanatory power ($R^2$) of the regression equation is reduced by 1. In particular, the number of data coordinates from the farthest side from the origin is reduced by 1.

If the calculated value of k/N is the same as or greater than the previously set ratio value, the step of computing the critical point representing a maximum straight-line segment using the calculated explanatory power ($R^2$) value of the regression equation may be included.

The previously set ratio value may range from 0.4 to 0.8, but is not limited thereto.

The present disclosure may further include the step of correcting the explanatory power ($R^2$) value of the regression equation computed in the Step 3) using a regression analysis method.

The correcting step may include the step of determining whether the difference between the explanatory power ($R^2$) value of the regression equation computed in the Step 3) and the explanatory power ($R^2$) value (A2) of the regression equation between the coordinate closest to the origin and a coordinate closer to the origin than the coordinate farthest from the origin is the same as or smaller than a previously set comparison value.

The previously set comparison value may range from $10^{-1}$ to $10^{-5}$, but is not limited thereto.

If the difference between the explanatory power (R) value of the regression equation computed in the Step 3) and the explanatory power ($R^2$) value (A2) of the regression equation between the coordinate closest to the origin and a coordinate closer to the origin than the coordinate farthest from the origin is the same as or smaller than the previously set comparison value, the step of computing the critical point representing a maximum straight-line segment corrected using the explanatory power ($R^2$) value (A2) of the regression equation may be included.

If the difference between the explanatory power (R) value of the regression equation computed in the Step 3) and the explanatory power ($R^2$) value (A2) of the regression equation between the coordinate closest to the origin and a coordinate m points closer to the origin than the coordinate farthest from the origin is greater than the previously set comparison value, the step of substituting the explanatory power ($R^2$) value (A2) of the regression equation may be included by calculating the explanatory power ($R^2$) value of the regression equation between the coordinate closest to the origin and a coordinate m+1 points closer to the origin than the coordinate farthest from the origin.

In this case, m is an integer, and $1 \leq m \leq N$.

The number of side chains of a polymer may be computed using the critical point computed in accordance with the method for analyzing side chains of a polymer according to the present disclosure.

The method for computing the number of side chains of a polymer can be selected among methods commonly used in the art.

For example, as shown in FIG. 1, the number of side chains of a polymer may be computed using the area generated based on the difference from a reference graph after a critical point by comparing a log scale graph of a polymer having side chains with a log scale graph of a linear polymer as a reference.

Figure 2:
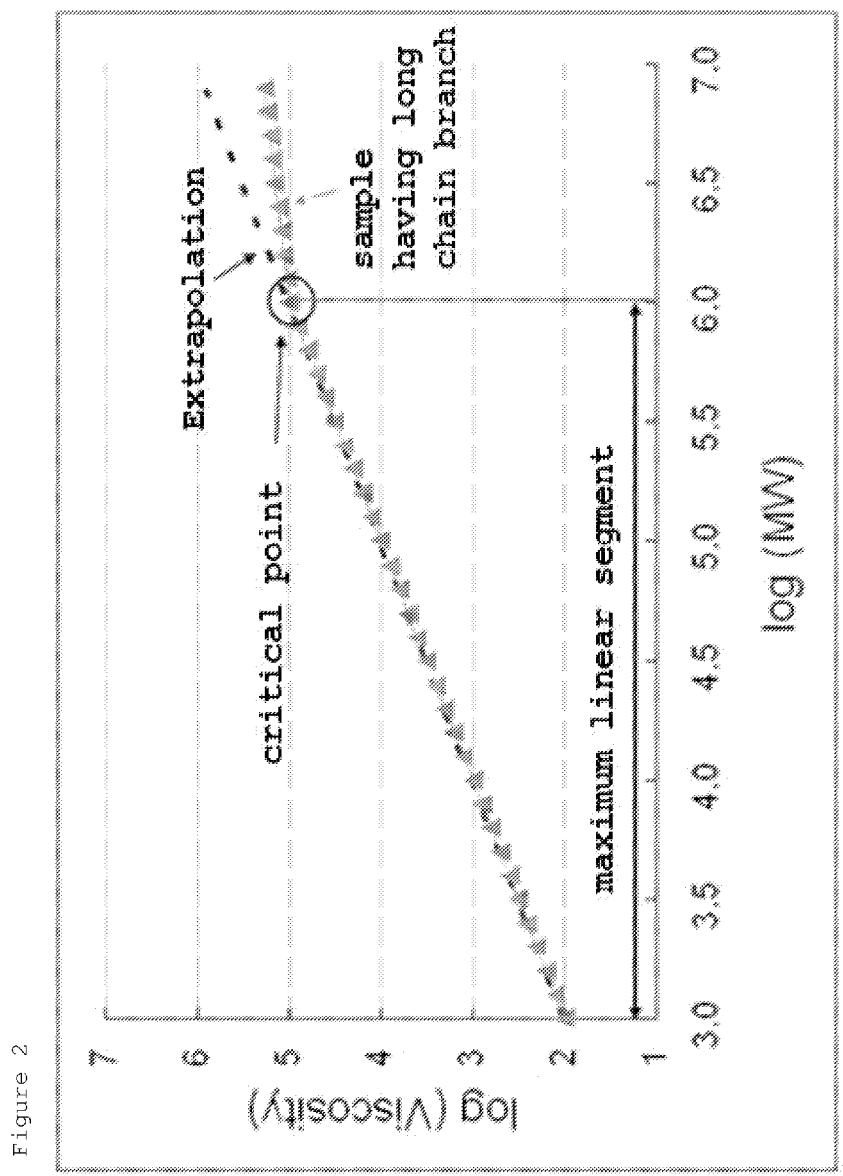
FIG. 2 is a diagram that shows a method for calculating the number of side chains of a polymer when there is no reference linear polymer.

Meanwhile, when there is no linear polymer that can be used as a reference, as shown in FIG. 2, a maximum linear segment is selected by obtaining a critical point representing a maximum straight-line segment in which the slope rapidly decreases in a log scale graph, and the slope in this area is calculated. Using the slope of the maximum linear segment, extrapolation is conducted beyond the critical point, which represents a maximum straight-line segment. Using this as a reference, the area for the difference from the log scale graph of a polymer having side chains is calculated, and the number of side chains of a polymer is computed based on the calculated area.

A graph extrapolated by extending the straight line between the origin and the critical point is made as a reference graph in the log scale graph of a polymer having side chains, and the number of side chains of a polymer is calculated using the area generated based on the difference from the reference graph after the critical point.

The side chain of a polymer means a branch that branches from the main chain of a polymer, and the length thereof is not particularly limited.

Of the above side chains, a long chain branch (LCB) may affect the strength of a polymer, the glass temperature, or the like.

Meanwhile, of the above side chains, an atactic short chain branch may reduce the strength of a polymer, since it makes the arrangement of a polymer poor.

When a polymer has a small number of side chains, the log scale graph of the molecular weight and the intrinsic viscosity of a polymer shows almost perfect linearity.

A polymer having a small number of side chains refers to a polymer in which a critical point representing a maximum straight-line segment is hard to find intuitively in the log scale graph of the molecular weight and the intrinsic viscosity of a polymer. The number of side chains is not particularly limited, for example, the number may range from 0.01 to 1 per 1,000 carbon atoms in the main chain.

Figure 3:
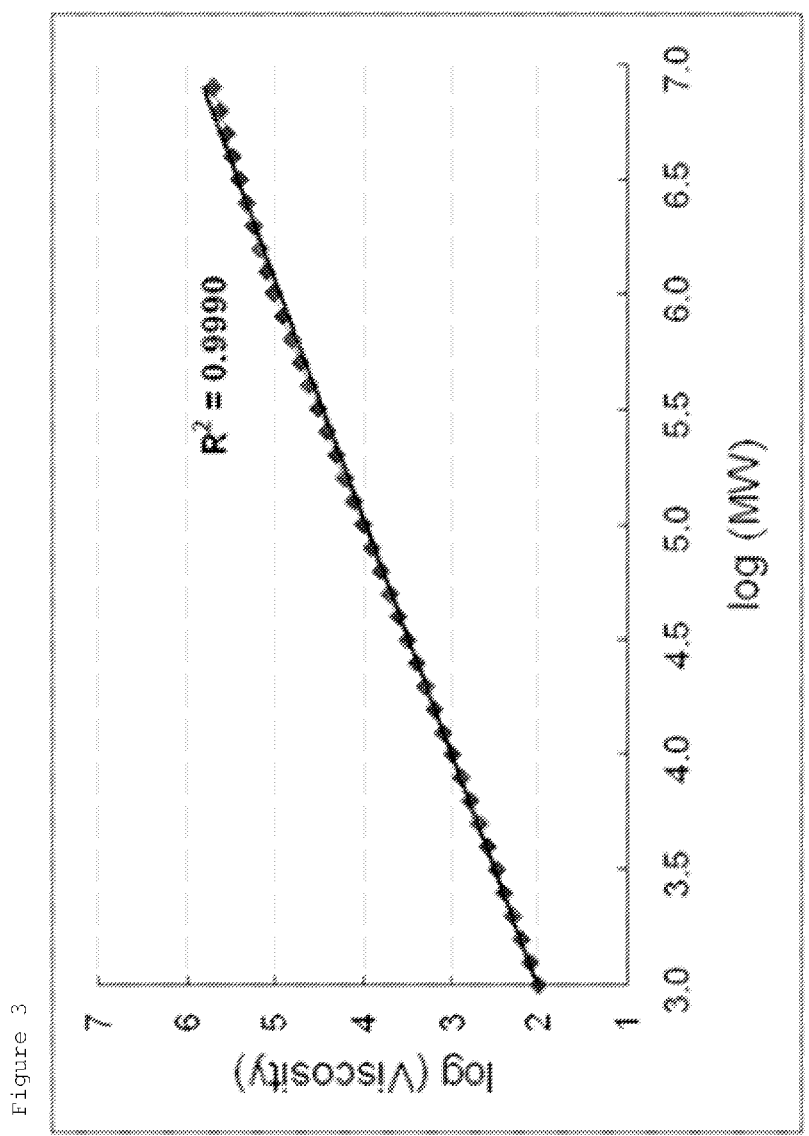
FIG. 3 is a log scale graph of the molecular weight and the intrinsic viscosity of a polymer in which the explanatory power ($R^2$) of a regression equation is 0.9990.

For example, if the log scale graph of the molecular weight and the intrinsic viscosity of a polymer shown in FIG. 3 is examined, it can be seen that a nearly linear graph, in which the explanatory power ($R^2$) of a regression equation is 0.9990, appears.

When the number of side chains of a polymer is small, as shown by the diagram in FIG. 3, the entire measured segment of the graph is already close to a linear shape, therefore, as the number of side chains of a polymer decreases, the error associated with the critical point, which represents a maximum straight-line segment, increases.

However, in the method for analyzing side chains of a polymer according to one embodiment of the present disclosure, there are advantages such that a critical point representing a maximum straight-line segment with high accuracy can be found even when the number of side chains of a polymer is small.

The method for analyzing side chains of a polymer according to one embodiment of the present disclosure, which is described in FIG. 4 to FIG. 6 and FIG. 10, is as follows.

Figure 4:
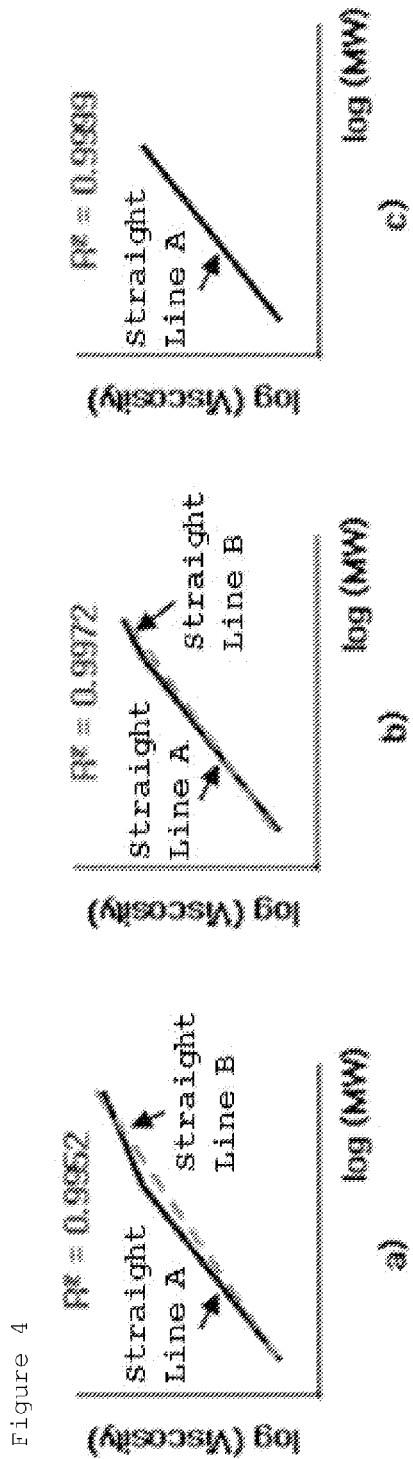
FIG. 4 is a diagram that describes a method for analyzing side chains of a polymer according to one embodiment of the present disclosure.

As shown by the diagram in FIG. 4, the log scale graph of a polymer having side chains is largely formed with two straight lines having different slopes, with a critical point representing a maximum straight-line segment as the center. One straight line is Straight Line A, which represents a maximum linear segment, and the other straight line is Straight Line B, which is an area in which the slope decreases compared with that of the maximum linear segment after the critical point representing a maximum straight-line segment. The linearity of the entire segment is mostly affected by Straight Line A, and the entire segment has reduced linearity compared with Straight Line A due to the appearance of the Straight Line B after the critical point representing a maximum straight-line segment. Therefore, if there are no data belonging to Straight Line B, the linearity of the entire segment will be exactly the same as the linearity of the maximum linear segment.

As a result, if the maximum value of Log (Mw) is decremented by intervals of one in the entire segment, linearity increases, since the entire segment is closer to Straight Line A, which is a maximum linear segment, with the data belonging to Straight Line B being decremented by intervals of one. The explanatory power ($R^2$) of the regression equation represents linearity; therefore, the explanatory power ($R^2$) value of the regression equation will represent the maximum value close to 1 when the maximum value of Log (Mw) reaches the critical point representing a maximum straight-line segment.

Figure a) of FIG. 4 is a log scale graph of the molecular weight and the intrinsic viscosity of a polymer for which the explanatory power ($R^2$) of a regression equation is 0.9952, and in Figure b), if the maximum value of Log (Mw) is decremented, linearity generally increases since the area of Straight Line B is gradually reduced in the entire segment, and the explanatory power ($R^2$) of the regression equation at this time gradually increases to approach 1.0. Figure c) is a case in which a critical point representing a maximum straight-line segment is reached by reducing the maximum value of Log (Mw), and the explanatory power ($R^2$) of the regression equation in this segment has a maximum value close to 1.0, since only Straight Line A exists precisely in the entire segment.

According to one embodiment of the present disclosure, there are advantages such that the presence or absence of side chains of a polymer can be seen even if the number of side chains of the polymer is small.

According to one embodiment of the present disclosure, there are advantages such that the number of side chains of a polymer can be computed even if the number of side chains of a polymer is small.

Figure 9:
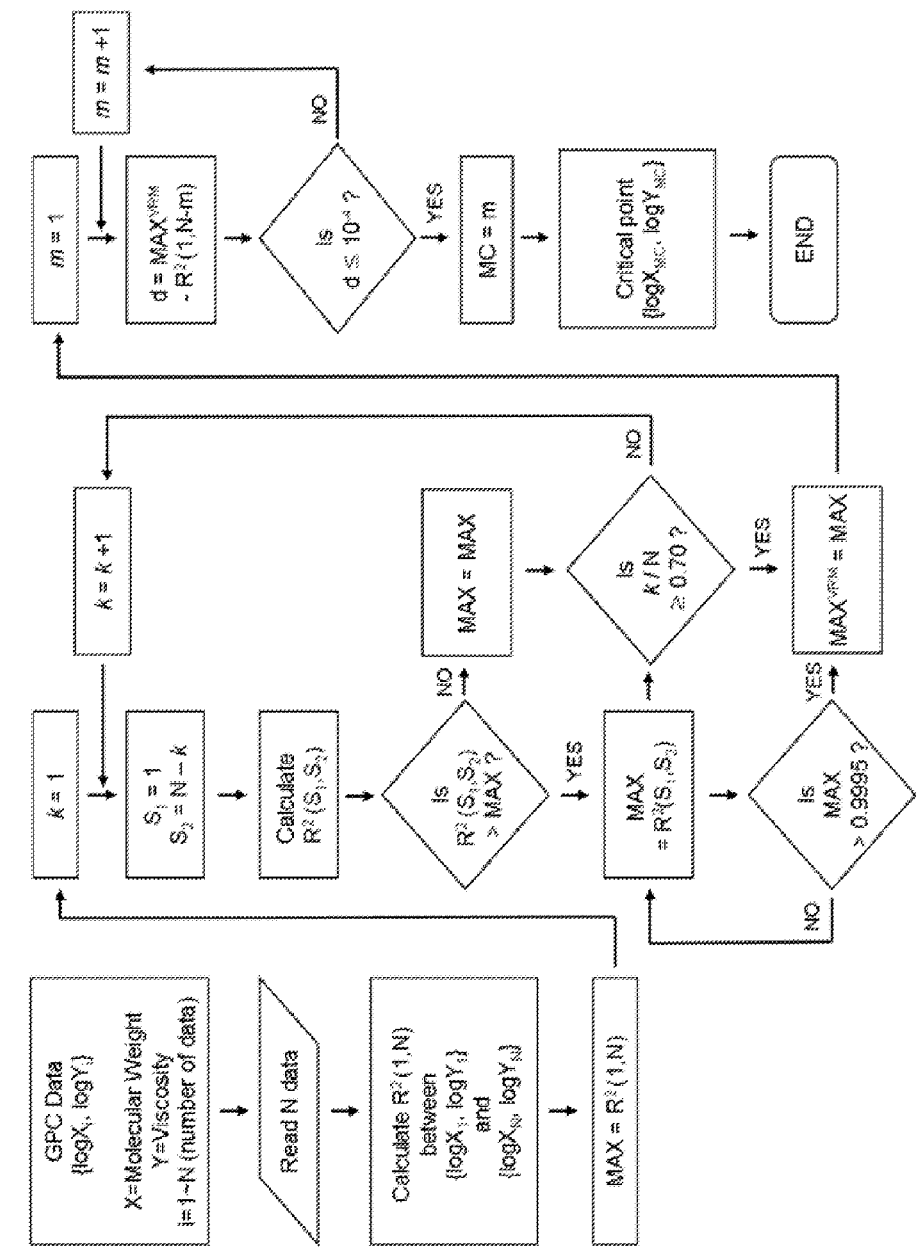
FIG. 9 is a flow chart illustrating the method for analyzing side chains of a polymer according to one embodiment of the present disclosure.

FIG. 9 is a flow chart illustrating the method for analyzing side chains of a polymer according to one embodiment of the present disclosure, but this is one example, and thus the present disclosure is not limited thereto.

The present disclosure provides a computer-readable recording medium on which a program for executing the method is recorded.

The present disclosure provides an apparatus for analyzing side chains of a polymer, including a display unit displaying a log scale graph of the molecular weight and the intrinsic viscosity of a polymer;

an analyzing unit calculating an explanatory power ($R^2$) value of a regression equation between a coordinate closest to an origin and a coordinate farthest from the origin or a coordinate closer to the origin than the coordinate farthest from the origin, among the total coordinates of the graph, and determining whether the value exceeds a previously set reference explanatory power ($R^2$) value of a regression equation; and a first computation unit computing a critical point representing a maximum straight-light segment using the calculated explanatory power ($R^2$) value of the regression equation, if the calculated explanatory power ($R^2$) value of the regression equation exceeds the previously set reference explanatory power ($R^2$) value of the regression equation.

The analyzing unit sets the explanatory power ($R^2$) value of the regression equation between the coordinate closest to the origin and the coordinate farthest from the origin as an initial value (A1), calculates the explanatory power ($R^2$) value of the regression equation between the coordinate closest to the origin and a coordinate closer to the origin than the coordinate farthest from the origin, among the total coordinates of the graph, and determines whether the value is greater than the initial value (A1), and substitutes the initial value (A1) for the calculated explanatory power ($R^2$) value of the regression equation, if the calculated explanatory power ($R^2$) value of the regression equation is greater than the initial value (A1).

The analyzing unit may include a first calculation unit calculating the explanatory power ($R^2$) value of the regression equation between the coordinate closest to the origin and a coordinate k points closer to the origin than the coordinate farthest from the origin when the number of coordinate data in the graph is N. In this case, k is an integer, and $1 \leq k \leq N$.

The analyzing unit may include a comparison unit calculating the value of k/N and determining whether the value is the same as or greater than a previously set ratio value, if the explanatory power ($R^2$) value of the regression equation calculated in the calculation unit does not exceed the previously set reference explanatory power ($R^2$) value of the regression equation.

The analyzing unit may include a second calculation unit calculating the explanatory power ($R^2$) value of the regression equation between the coordinate closest to the origin and a coordinate k+1 points closer to the origin than the coordinate farthest from the origin, if the value of k/N calculated in the comparison unit is smaller than the previously set ratio value.

The analyzing unit may include a second computation unit computing the critical point representing a maximum straight-line segment using the calculated explanatory power ($R^2$) value of the regression equation, if the value of k/N calculated in the comparison unit is the same as or greater than the previously set ratio value.

A correction unit correcting the explanatory power ($R^2$) value of the regression equation computed in the first computation unit may be further included.

The correction unit determines whether the difference between the explanatory power ($R^2$) value of the regression equation computed in the first computation unit and the explanatory power ($R^2$) value of the regression equation between the coordinate closest to the origin and a coordinate closer to the origin than the coordinate farthest from the origin is the same as or smaller than the previously set comparison value.

Hereinafter, the present disclosure will be described in detail with reference to examples. However, it is to be understood that the following examples are for illustrative purposes only, and the scope of the present disclosure includes the scope described in the following claims, and substitutions and modifications thereof, and is not limited to the scope of the examples.

EXAMPLES

Experimental Examples (1) Validity Verification Through Error Estimation (Explanatory Power ($R^2$) of Regression Equation is 0.9858)

Figure 5:
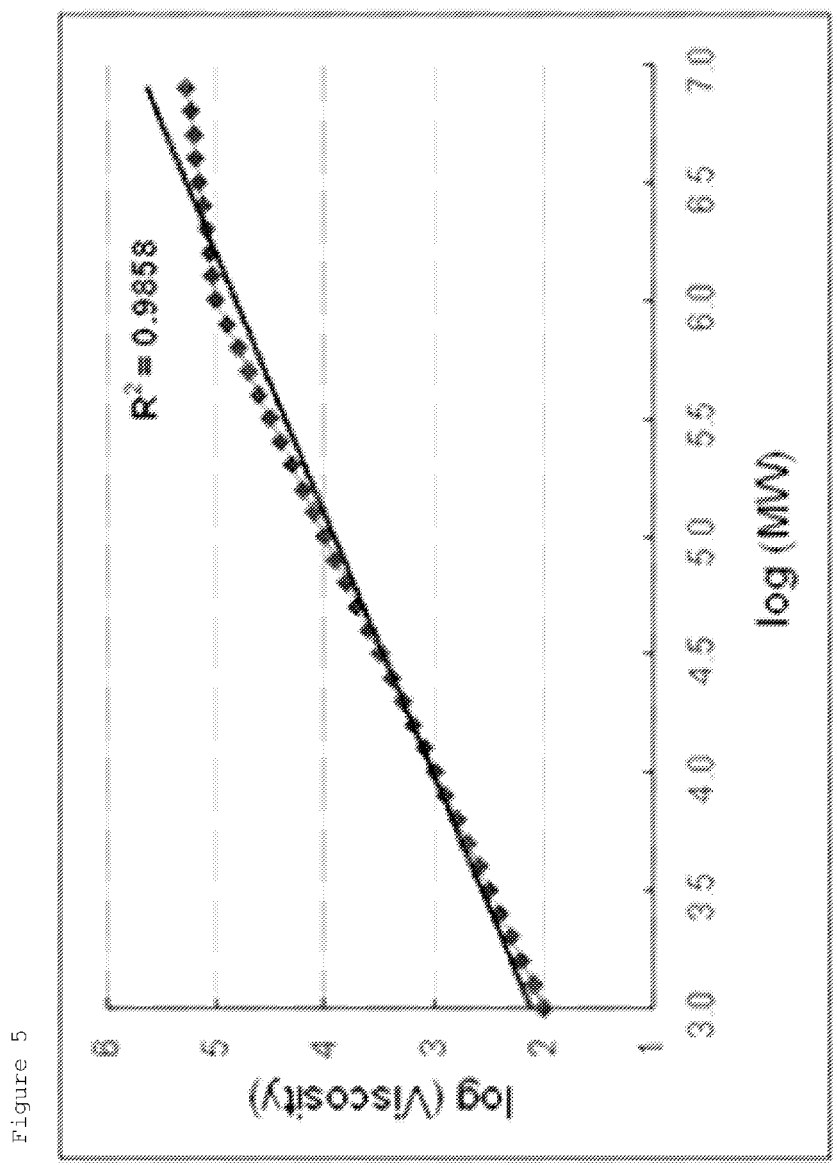
FIG. 5 is a log scale graph of the molecular weight and the intrinsic viscosity of a polymer in which the explanatory power ($R^2$) of a regression equation is 0.9858.

The graph shown in FIG. 5 is a graph for which the explanatory power ($R^2$) of the regression equation is 0.9858, and the critical point representing a maximum straight-line segment is Log (Mw)=6.0.

Figure 6:
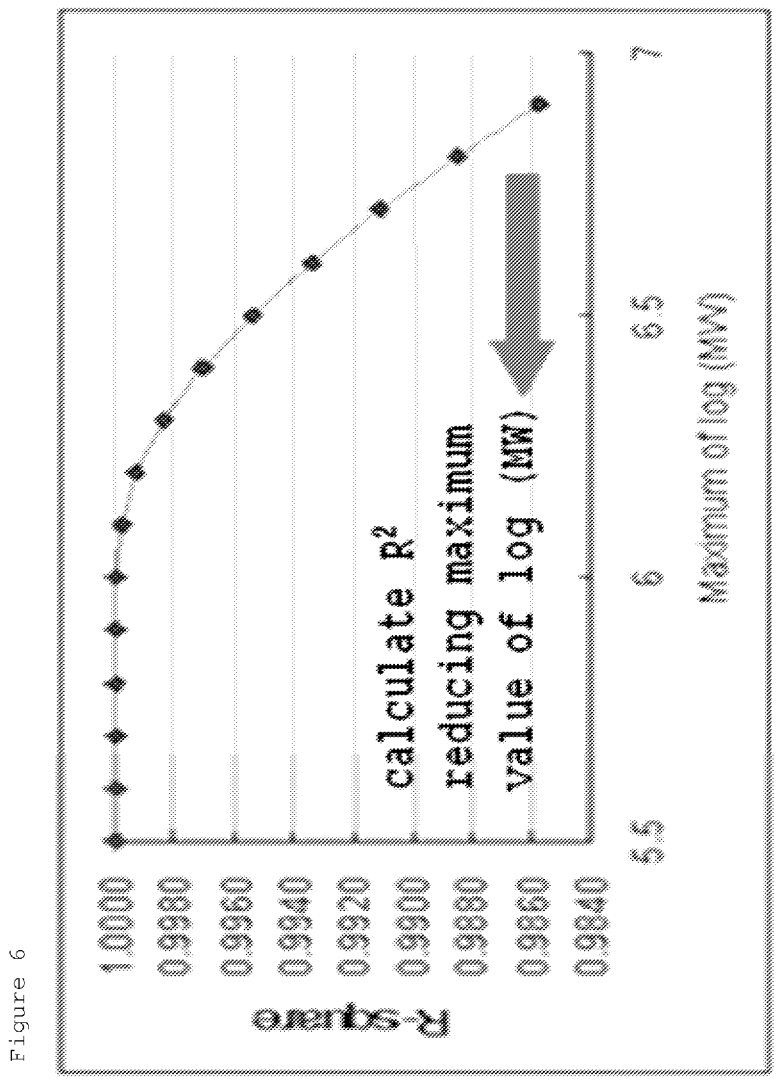
FIG. 6 is a graph of the explanatory power ($R^2$) of a regression equation computed using the method for analyzing side chains of a polymer according to one embodiment of the present disclosure and the maximum value of Log (Mw) corresponding to the graph in FIG. 5.

The result of measuring the explanatory power ($R^2$) of the regression equation for the above graph by reducing the maximum value of Log (Mw) through the method for analyzing side chains of a polymer according to the present disclosure is shown by the diagram in FIG. 6, and as can be seen from the figure, if the maximum value of Log (Mw) is reduced, the explanatory power ($R^2$) of the regression equation gradually increases due to the increase in linearity across the entire segment. Then the value of Log (Mw) reaches 6.0, and the explanatory power ($R^2$) of the regression equation becomes 1.0, and remains at the value of 1.0 after that.

In other words, at Log (Mw) of 6.0, which is the critical point representing a maximum straight-line segment, the explanatory power ($R^2$) of the regression equation is at a maximum.

As a result, it can be seen that a critical point representing a maximum straight-line segment is accurately found through the method for analyzing side chains of a polymer according to the present disclosure.

(2) Validity Verification Through Error Estimation (Explanatory Power ($R^2$) of Regression Equation is 0.9990)

Figure 7:
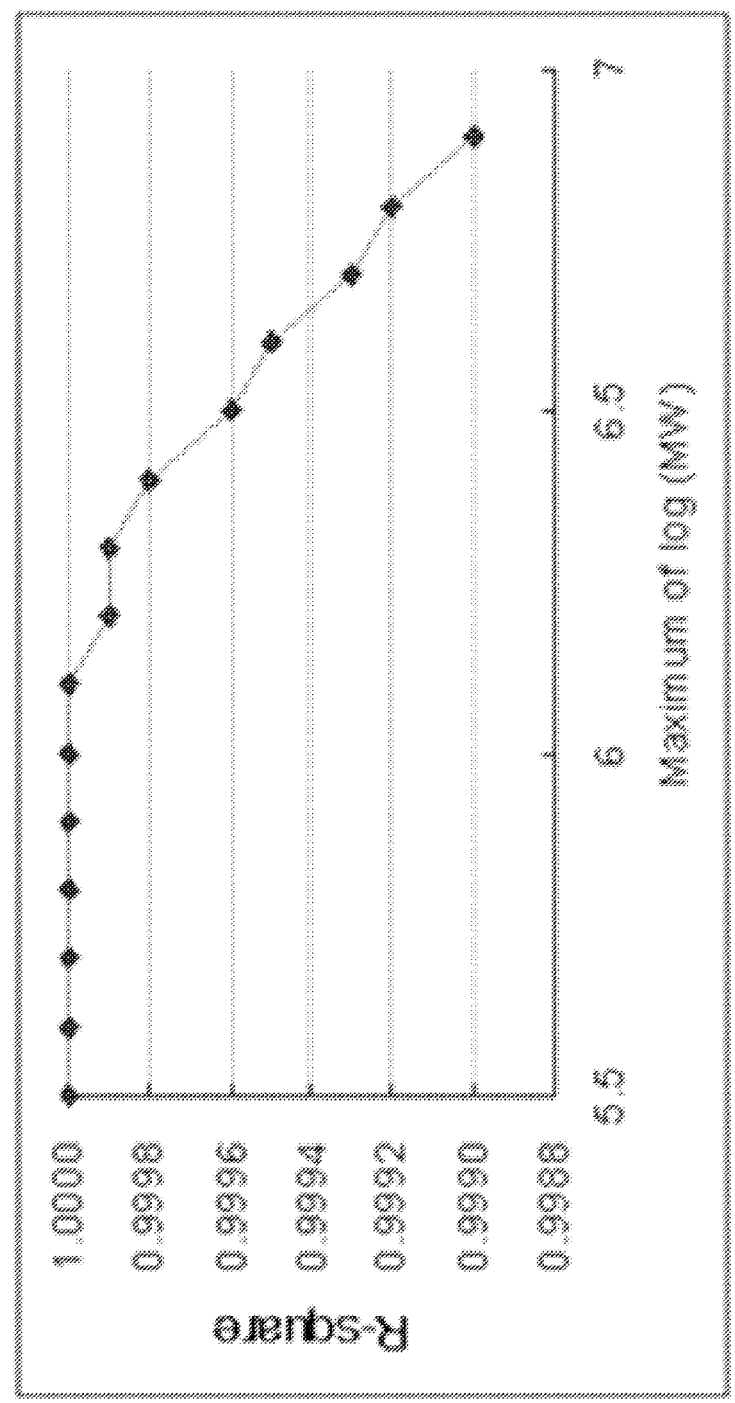
FIG. 7 is a graph of the explanatory power ($R^2$) of a regression equation computed using the method for analyzing side chains of a polymer according to one embodiment of the present disclosure and the maximum value of Log (Mw) corresponding to the graph in FIG. 3.

The graph shown in FIG. 3 is a graph for which the explanatory power ($R^2$) of the regression equation is 0.9990, and the critical point representing a maximum straight-line segment is Log (Mw) of 6.0. The result of measuring the explanatory power ($R^2$) of the regression equation for the above group by reducing the maximum value of Log (Mw) through the method for analyzing side chains of a polymer according to the present disclosure is shown by the diagram in FIG. 7, and the calculated critical point representing a maximum straight-line segment is Log (Mw) of 6.1.

This means that the relative error is 1.7%, and thus a critical point with high accuracy was able to be obtained with a relatively small error range.

(3) Validity Verification Through Error Estimation

Figure 8:
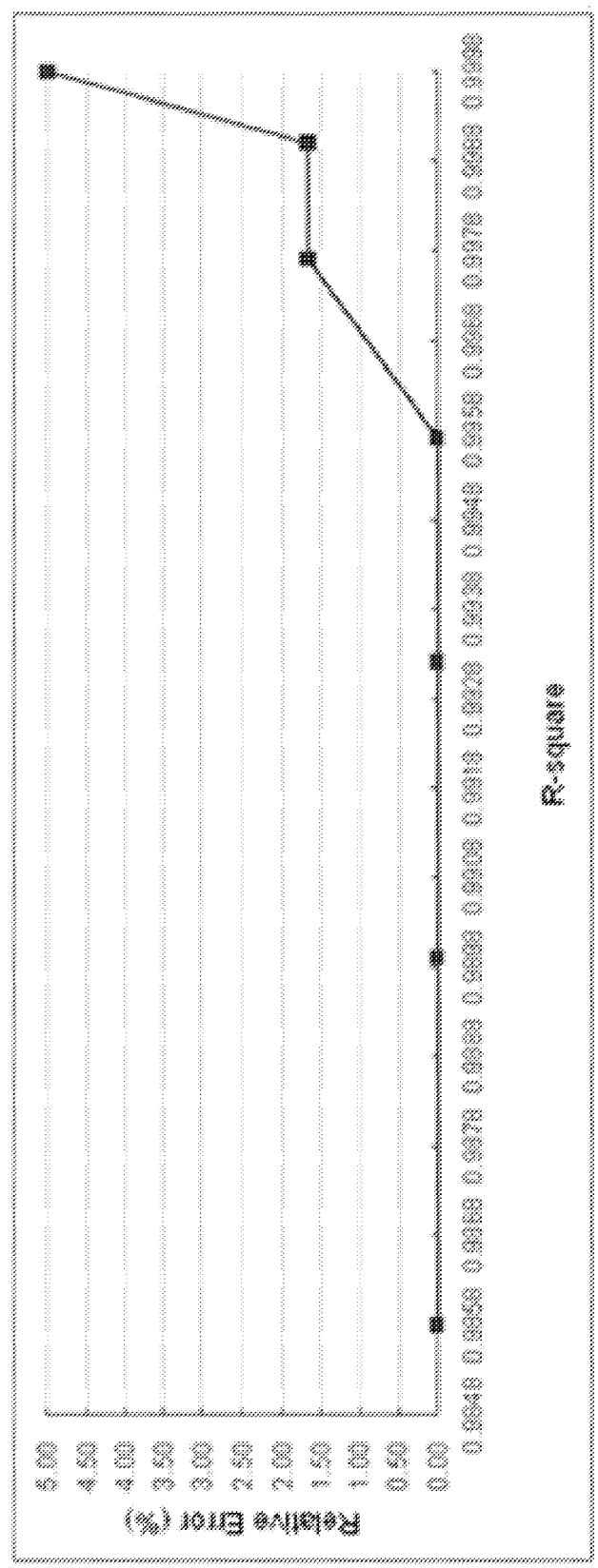
FIG. 8 is a graph of the explanatory power ($R^2$) of a regression equation calculated using the method for analyzing side chains of a polymer according to one embodiment of the present disclosure and a relative error.

The same experiments as those of (1) and (2) were also performed for regression equation explanatory powers ($R^2$) of 0.9898, 0.9933, 0.9958, 0.9978 and 0.9998, and the graph of relative errors for regression equation explanatory powers ($R^2$) is shown in FIG. 8.

The relative error is 0% to the point at which the explanatory power ($R^2$) of the regression equation is 0.9958, therefore, it can be seen that the critical point for the maximum linear segment is accurately calculated. In addition, when the explanatory power ($R^2$) of the regression equation is greater than 0.9958, the relative error starts to occur, and the relative error reaches up to 5% when the entire segment is almost linear (the explanatory power ($R^2$) of the regression equation=0.9998).

As a result, even when the entire segment is almost linear, it can be seen that the critical point for the maximum linear segment is accurately calculated within the relative error range of maximum 5%.

The invention claimed is:

1. A method for analyzing side chains of a polymer, the method comprising the steps of:
   1) displaying a log scale graph of the molecular weight and the intrinsic viscosity of a polymer;
   2) calculating an explanatory power ($R^2$) value of a regression equation between a coordinate closest to an origin and a coordinate farthest from the origin or a coordinate closer to the origin than the coordinate farthest from the origin, among the total coordinates of the graph, and determining whether the value exceeds a previously set reference explanatory power ($R^2$) value of a regression equation; and
   3) computing a critical point representing a maximum straight-line segment using the calculated explanatory power ($R^2$) value of the regression equation, if the calculated explanatory power ($R^2$) value of the regression equation exceeds the previously set reference explanatory power ($R^2$) value of the regression equation.

2. The method for analyzing side chains of a polymer of claim 1,
   wherein the Step 2) includes the step of calculating the explanatory power ($R^2$) value of the regression equation between the coordinate closest to the origin and a coordinate k points closer to the origin than the coordinate farthest from the origin when the number of coordinate data in the graph is N, k is an integer, and $1 \leq k \leq N$.

3. The method for analyzing side chains of a polymer of claim 2,
   wherein the step of calculating the value of k/N and determining whether the value is the same as or greater than a previously set ratio value is included, if the explanatory power ($R^2$) value of the regression equation calculated in the Step 2) does not exceed the previously set reference explanatory power ($R^2$) value of the regression equation.

4. The method for analyzing side chains of a polymer of claim 3,
   wherein the step of calculating the explanatory power ($R^2$) value of the regression equation between a coordinate closest to the origin and a coordinate k+1 points closer to the origin than the coordinate farthest from the origin is included, if the calculated value of k/N is smaller than the previously set ratio value.

5. The method for analyzing side chains of a polymer of claim 3,
   wherein the step of computing the critical point representing a maximum straight-line segment using the calculated explanatory power ($R^2$) value of the regression equation is included, if the calculated value of k/N is the same as or greater than the previously set ratio value.

6. The method for analyzing side chains of a polymer of claim 1, further comprising the step of:
   correcting the explanatory power ($R^2$) value of the regression equation computed in the Step 3) using a regression analysis method.

7. The method for analyzing side chains of a polymer of claim 6,
   wherein the correcting step includes the step of determining whether the difference between the explanatory power ($R^2$) value of the regression equation computed in the Step 3) and the explanatory power ($R^2$) value of the regression equation between the coordinate closest to the origin and a coordinate closer to the origin than the coordinate farthest from the origin is the same as or smaller than a previously set comparison value.

8. The method for analyzing side chains of a polymer of claim 1,
   wherein the Step 2) includes the steps of setting the explanatory power ($R^2$) value of the regression equation between the coordinate closest to the origin and the coordinate farthest from the origin as an initial value (A1);
   calculating the explanatory power ($R^2$) value of the regression equation between the coordinate closest to the origin and a coordinate closer to the origin than the coordinate farthest from the origin, among the total coordinates of the graph, and determining whether the value is greater than the initial value (A1); and
   substituting the initial value (A1) for the calculated explanatory power ($R^2$) value of the regression equation with the calculated explanatory power ($R^2$) value of the regression equation, if the calculated explanatory power ($R^2$) value of the regression equation is greater than the initial value (A1).

9. A non-transitory computer-readable recording medium on which a program for executing the method of claim 1 is recorded.

10. An apparatus for analyzing side chains of a polymer comprising:
    a display unit displaying a log scale graph of the molecular weight and the intrinsic viscosity of a polymer;
    an analyzing unit calculating an explanatory power ($R^2$) value of a regression equation between a coordinate closest to an origin and a coordinate farthest from the origin or a coordinate closer to the origin than the coordinate farthest from the origin, among the total coordinates of the graph, and determining whether the value exceeds a previously set reference explanatory power ($R^2$) value of a regression equation; and
    a first computation unit computing a critical point representing a maximum straight-light segment using the calculated explanatory power ($R^2$) value of the regression equation, if the calculated explanatory power ($R^2$) value of the regression equation exceeds the previously set reference explanatory power ($R^2$) value of the regression equation.

11. The apparatus for analyzing side chains of a polymer of claim 10,
   wherein the analyzing unit includes a first calculation unit calculating the explanatory power ($R^2$) value of the regression equation between the coordinate closest to the origin and a coordinate k points closer to the origin than the coordinate farthest from the origin when the number of coordinate data in the graph is N, k is an integer, and $1 \leq k \leq N$.

12. The apparatus for analyzing side chains of a polymer of claim 11,
   wherein the analyzing unit includes a comparison unit calculating the value of k/N and determining whether the value is the same as or greater than a previously set ratio value, if the explanatory power ($R^2$) value of the regression equation calculated in the calculation unit does not exceed the previously set reference explanatory power ($R^2$) value of the regression equation.

13. The apparatus for analyzing side chains of a polymer of claim 12,
   wherein the analyzing unit includes a second calculation unit calculating the explanatory power ($R^2$) value of the regression equation between the coordinate closest to the origin and a coordinate k+1 points closer to the origin than the coordinate farthest from the origin, if the value of k/N calculated in the comparison unit is smaller than the previously set ratio value.

14. The apparatus for analyzing side chains of a polymer of claim 12,
   wherein the analyzing unit includes a second computation unit computing the critical point representing a maximum straight-line segment using the calculated explanatory power ($R^2$) value of the regression equation, if the value of k/N calculated in the comparison unit is the same as or greater than the previously set ratio value.

15. The apparatus for analyzing side chains of a polymer of claim 10, further comprising:
   a correction unit correcting the explanatory power ($R^2$) value of the regression equation computed in the first computation unit.

16. The apparatus for analyzing side chains of a polymer of claim 15,
   wherein the correction unit determines whether the difference between the explanatory power ($R^2$) value of the regression equation computed in the first computation unit and the explanatory power ($R^2$) value of the regression equation between the coordinate closest to the origin and a coordinate closer to the origin than the coordinate farthest from the origin is the same as or smaller than a previously set comparison value.

17. The apparatus for analyzing side chains of a polymer of claim 10,
   wherein the analyzing unit sets the explanatory power ($R^2$) value of the regression equation between the coordinate closest to the origin and the coordinate farthest from the origin as an initial value (A1),
   calculates the explanatory power ($R^2$) value of the regression equation between the coordinate closest to the origin and a coordinate closer to the origin than the coordinate farthest from the origin, among the total coordinates of the graph, and determines whether the value is greater than the initial value (A1), and
   substitutes the initial value (A1) for the calculated explanatory power ($R^2$) value of the regression equation with the calculated explanatory power ($R^2$) value of the regression equation, if the calculated explanatory power ($R^2$) value of the regression equation is greater than the initial value (A1).

\* \* \* \* \*